United States Patent
Robertson

Patent Number: 5,964,394
Date of Patent: Oct. 12, 1999

[54] SURGICAL FASTENER APPLYING DEVICE

[75] Inventor: John C. Robertson, Cheshire, Conn.

[73] Assignee: United States Surgical Corporation, Norwalk, Conn.

[21] Appl. No.: 09/076,933

[22] Filed: May 13, 1998

Related U.S. Application Data

[63] Continuation of application No. 08/618,436, Mar. 15, 1996, Pat. No. 5,810,240.

[51] Int. Cl.$^6$ .................................................. A61B 17/068
[52] U.S. Cl. ..................... 227/176.1; 227/19; 227/175.2; 227/178.1
[58] Field of Search .................................. 227/19, 175.1, 227/176.1, 178.1, 179.1, 180.1, 175.2

[56] References Cited

U.S. PATENT DOCUMENTS

| | | |
|---|---|---|
| D. 273,513 | 4/1984 | Spreckelmeier . |
| D. 283,733 | 5/1986 | Rawson et al. . |
| 2,174,219 | 3/1939 | Balma . |
| 3,080,564 | 3/1963 | Strekopitov et al. . |
| 3,252,643 | 5/1966 | Strekopytov et al. . |
| 3,269,630 | 8/1966 | Fleischer . |
| 3,692,224 | 9/1972 | Astafiev et al. . |
| 3,795,034 | 3/1974 | Strekopytov et al. . |
| 3,822,818 | 7/1974 | Strekopytov et al. . |
| 4,296,881 | 10/1981 | Lee . |
| 4,305,539 | 12/1981 | Korolkov et al. . |
| 4,354,628 | 10/1982 | Green . |
| 4,378,901 | 4/1983 | Akopov et al. . |
| 4,383,634 | 5/1983 | Green . |
| 4,442,964 | 4/1984 | Becht . |
| 4,475,679 | 10/1984 | Fleury, Jr. . |
| 4,506,670 | 3/1985 | Crossley . |
| 4,508,253 | 4/1985 | Green . |
| 4,513,746 | 4/1985 | Aranyi et al. . |
| 4,527,724 | 7/1985 | Chow et al. . |
| 4,530,453 | 7/1985 | Green . |
| 4,566,620 | 1/1986 | Green et al. . |
| 4,568,009 | 2/1986 | Green . |
| 4,573,622 | 3/1986 | Green et al. . |
| 4,580,712 | 4/1986 | Green . |
| 4,585,153 | 4/1986 | Failla et al. . |
| 4,591,085 | 5/1986 | DiGiovanni . |
| 4,605,004 | 8/1986 | DiGiovanni et al. . |
| 4,606,344 | 8/1986 | DiGiovanni . |
| 4,606,345 | 8/1986 | Dorband et al. . |
| 4,607,636 | 8/1986 | Kula et al. . |
| 4,617,928 | 10/1986 | Alfrance . |
| 4,632,290 | 12/1986 | Green et al. . |
| 4,635,634 | 1/1987 | Santos . |
| 4,665,916 | 5/1987 | Green . |
| 4,684,051 | 8/1987 | Akopov et al. . |
| 4,714,187 | 12/1987 | Green . |
| 4,715,520 | 12/1987 | Roehr, Jr. et al. . |
| 4,728,020 | 3/1988 | Green et al. . |

(List continued on next page.)

FOREIGN PATENT DOCUMENTS

| | | |
|---|---|---|
| 0136950 | 4/1985 | European Pat. Off. . |
| 0220029 | 4/1987 | European Pat. Off. . |
| 0273468 | 7/1988 | European Pat. Off. . |
| 0537571 | 4/1993 | European Pat. Off. . |
| 2542188 | 9/1984 | France . |
| 2141066 | 12/1984 | United Kingdom . |

OTHER PUBLICATIONS

Information Booklet for Auto Suture, Poly CS–57, Disposable Surgical Stapler, 1988, USSC.

*Primary Examiner*—Scott A. Smith

[57] ABSTRACT

A fastener applying device for applying surgical fasteners to body tissue is provided. The fastener applying device includes an approximation mechanism having a single actuator to perform fast closure and incremental approximation of a cartridge carrier and anvil. The cartridge carrier and anvil can be approximated into a multiplicity of predetermined firing enabled positions. An adjustment member is operably associated with a firing mechanism of the device to vary the maximum stroke of a pusher bar. The adjustment member facilitates ejection of multiple size fasteners from the device.

9 Claims, 19 Drawing Sheets

U.S. PATENT DOCUMENTS

| | | |
|---|---|---|
| 4,741,336 | 5/1988 | Failla et al. . |
| 4,788,978 | 12/1988 | Strekopytov et al. . |
| 4,809,898 | 3/1989 | Gassner et al. . |
| 4,848,637 | 7/1989 | Pruitt . |
| 4,869,414 | 9/1989 | Green et al. . |
| 4,881,545 | 11/1989 | Isaacs et al. . |
| 4,915,100 | 4/1990 | Green . |
| 4,930,503 | 6/1990 | Pruitt . |
| 4,938,408 | 7/1990 | Bedi et al. . |
| 4,941,623 | 7/1990 | Pruitt . |
| 4,964,559 | 10/1990 | Deniega et al. . |
| 5,018,657 | 5/1991 | Pedlick et al. . |
| 5,027,834 | 7/1991 | Pruitt . |
| 5,071,052 | 12/1991 | Rodak et al. . |
| 5,100,042 | 3/1992 | Gravener et al. . |
| 5,116,349 | 5/1992 | Aranyi . |
| 5,137,198 | 8/1992 | Nobis et al. . |
| 5,190,203 | 3/1993 | Rodak . |
| 5,413,267 | 5/1995 | Solyntjes et al. . |
| 5,458,279 | 10/1995 | Plyley . |
| 5,470,006 | 11/1995 | Roadk . |
| 5,470,008 | 11/1995 | Rodak . |
| 5,470,009 | 11/1995 | Rodak . |
| 5,509,596 | 4/1996 | Green et al. . |

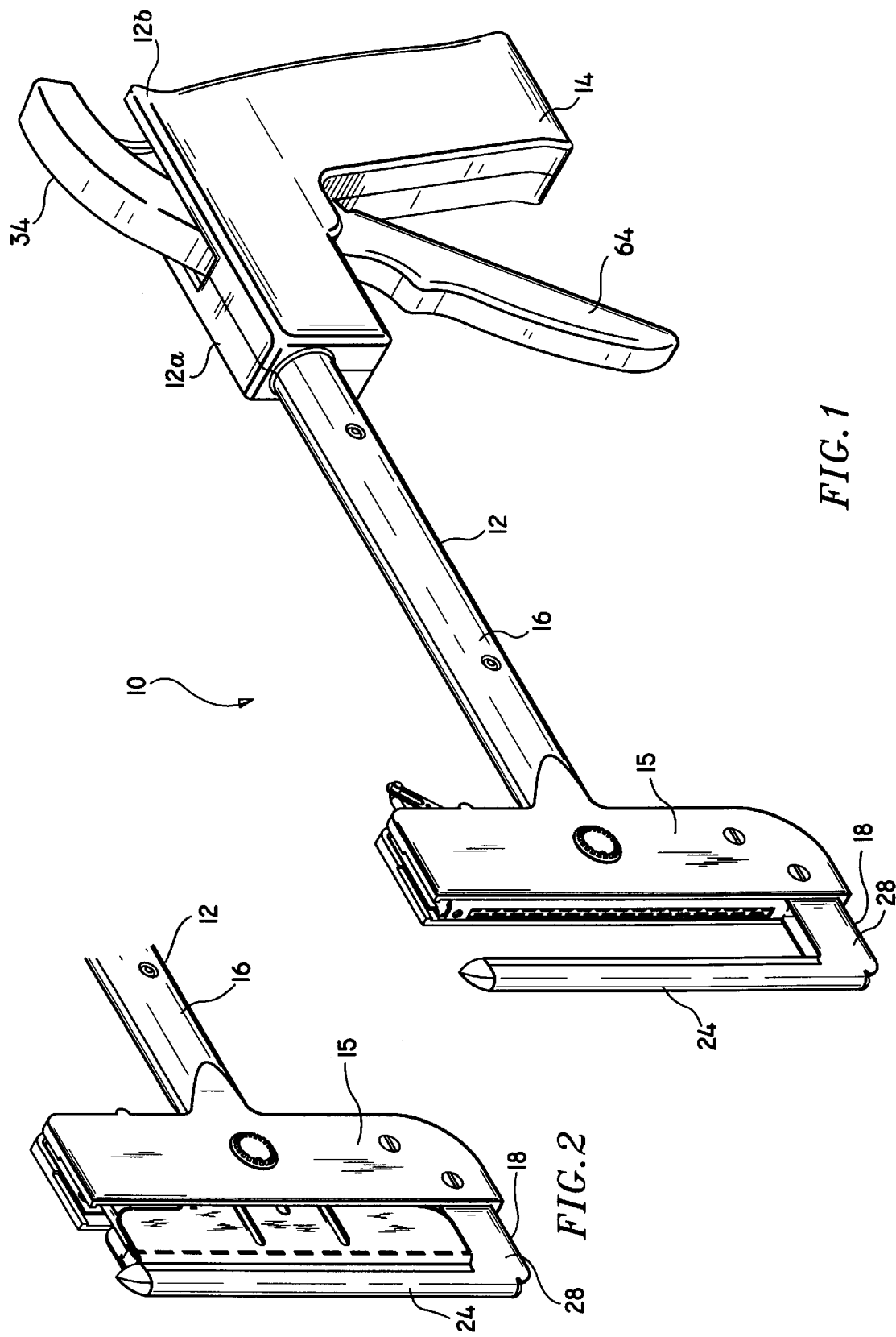

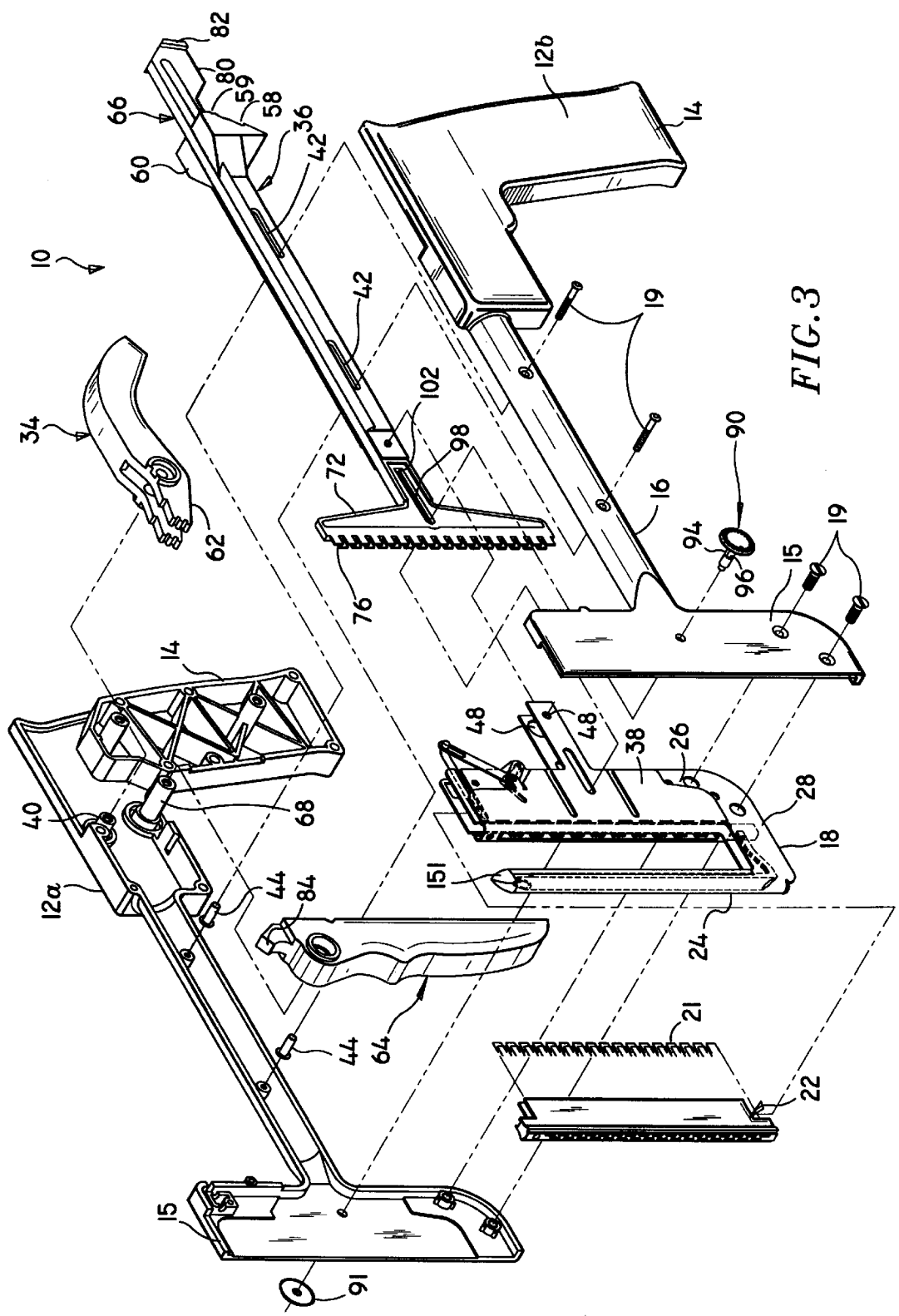

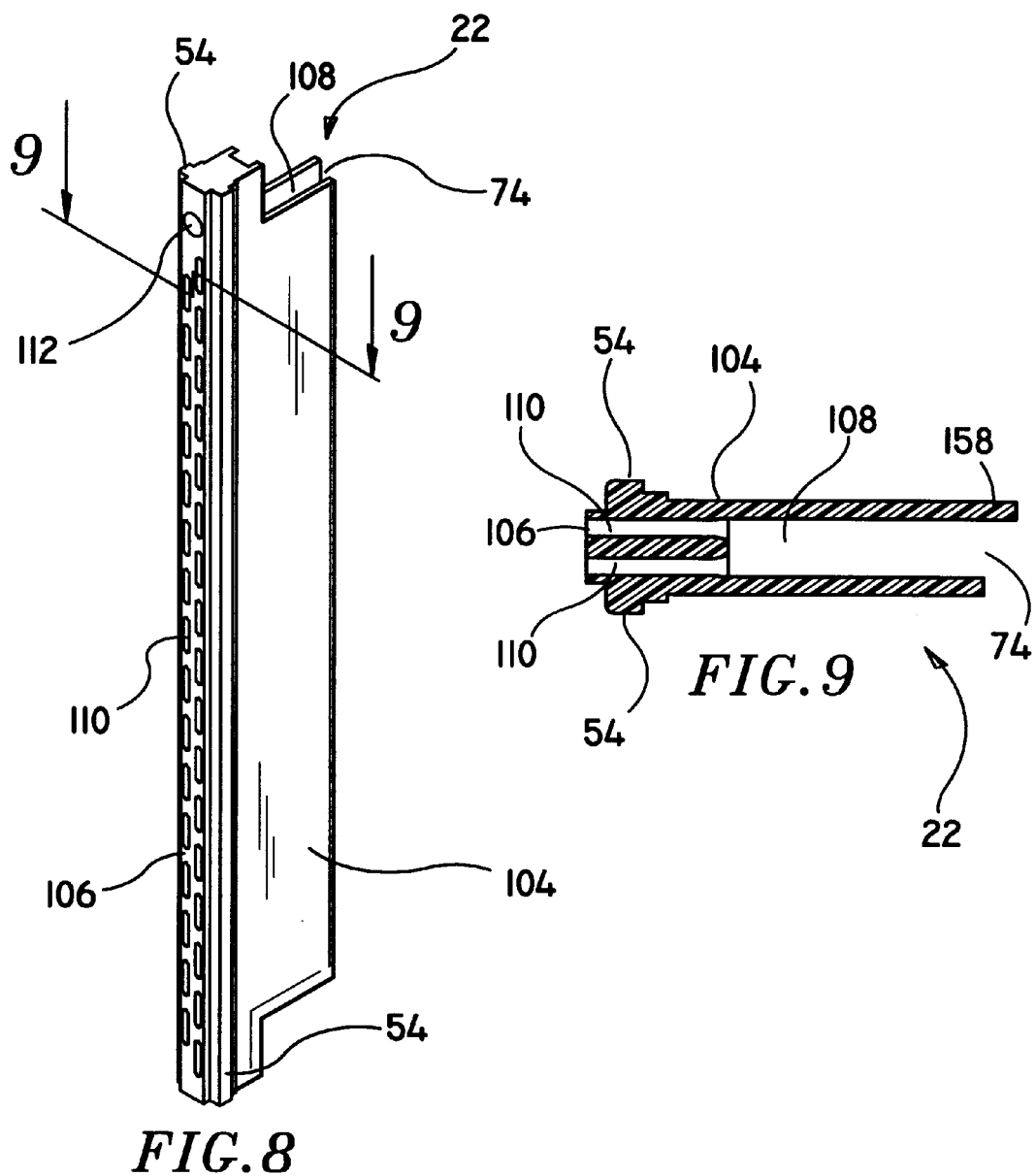

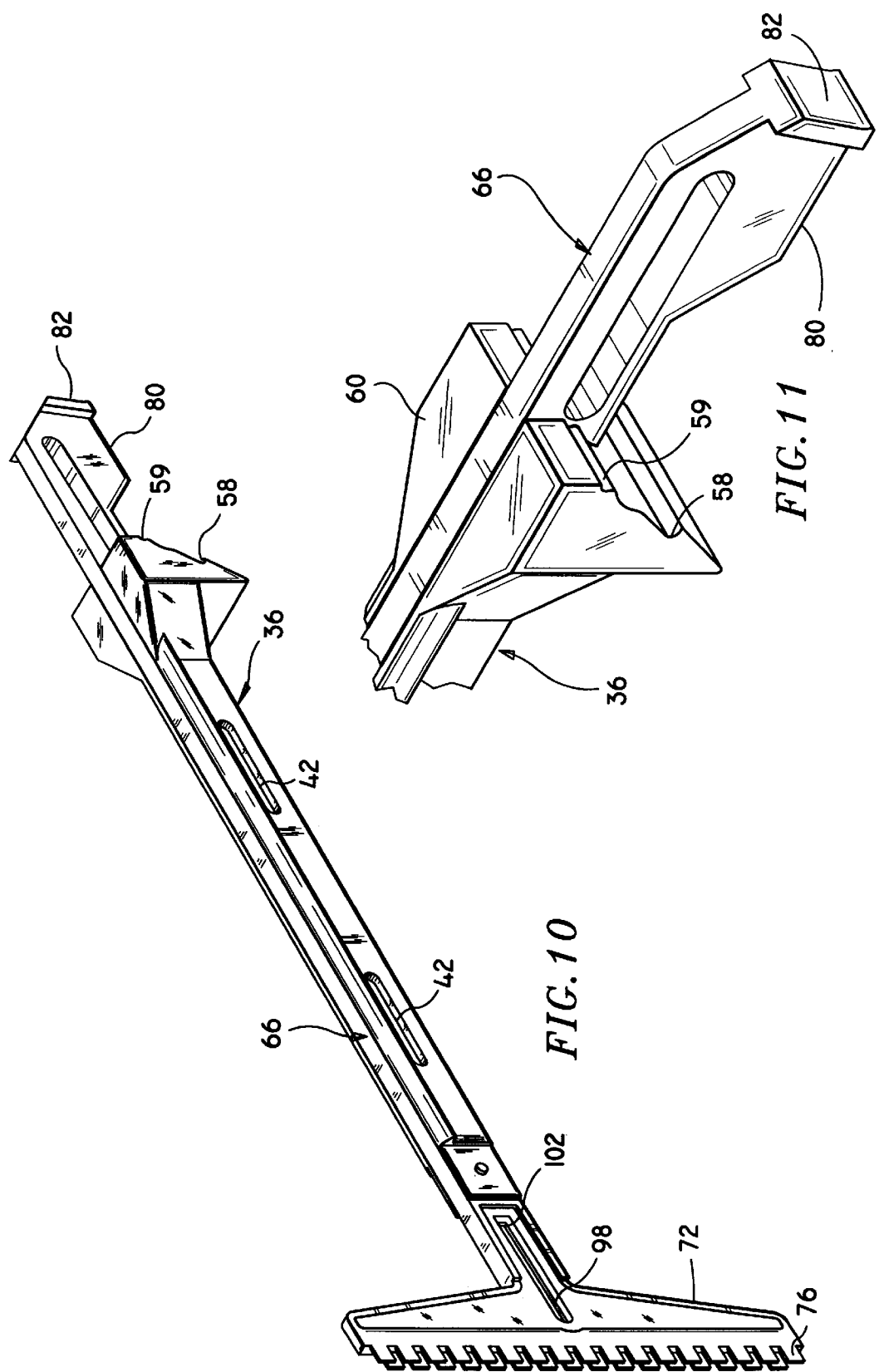

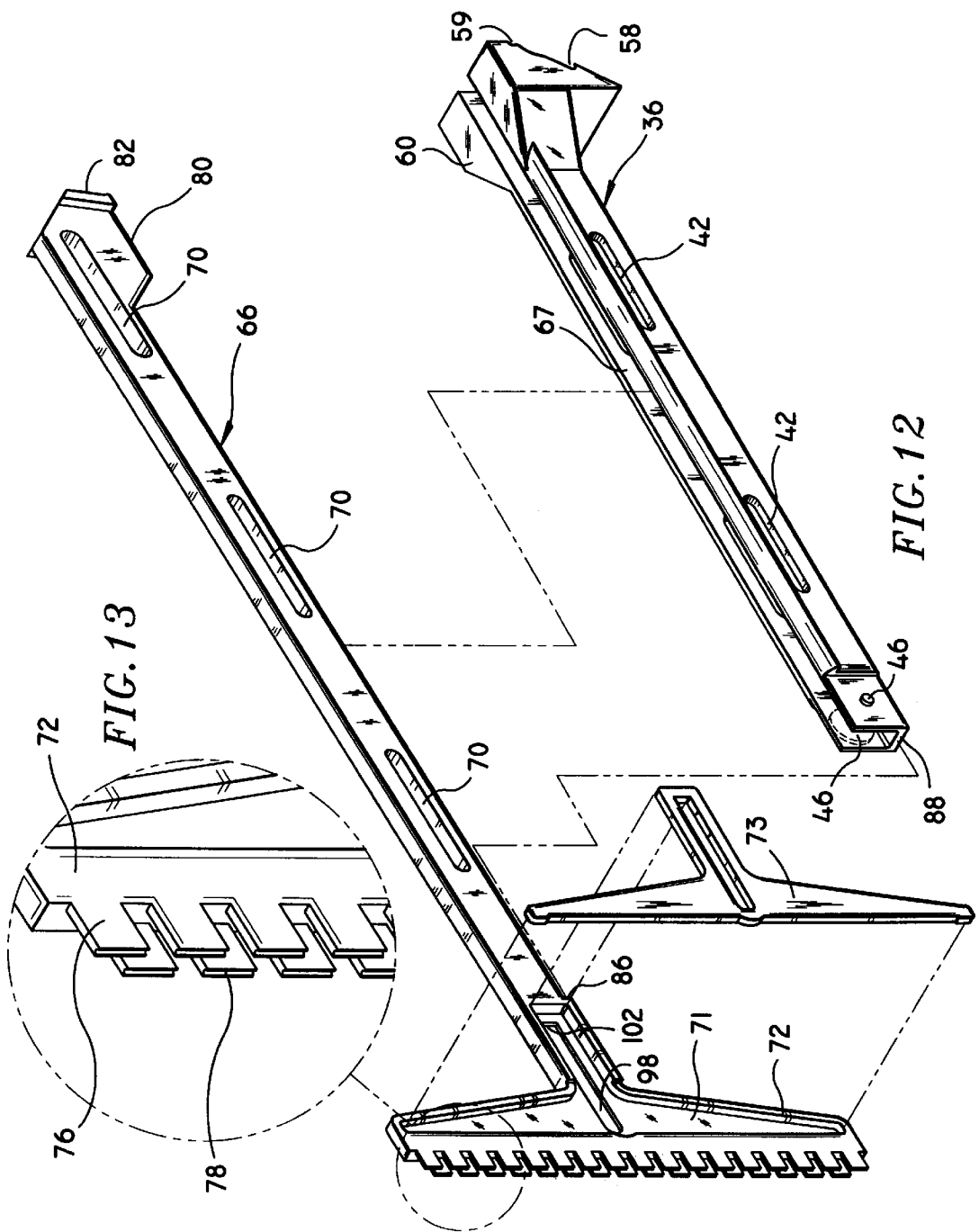

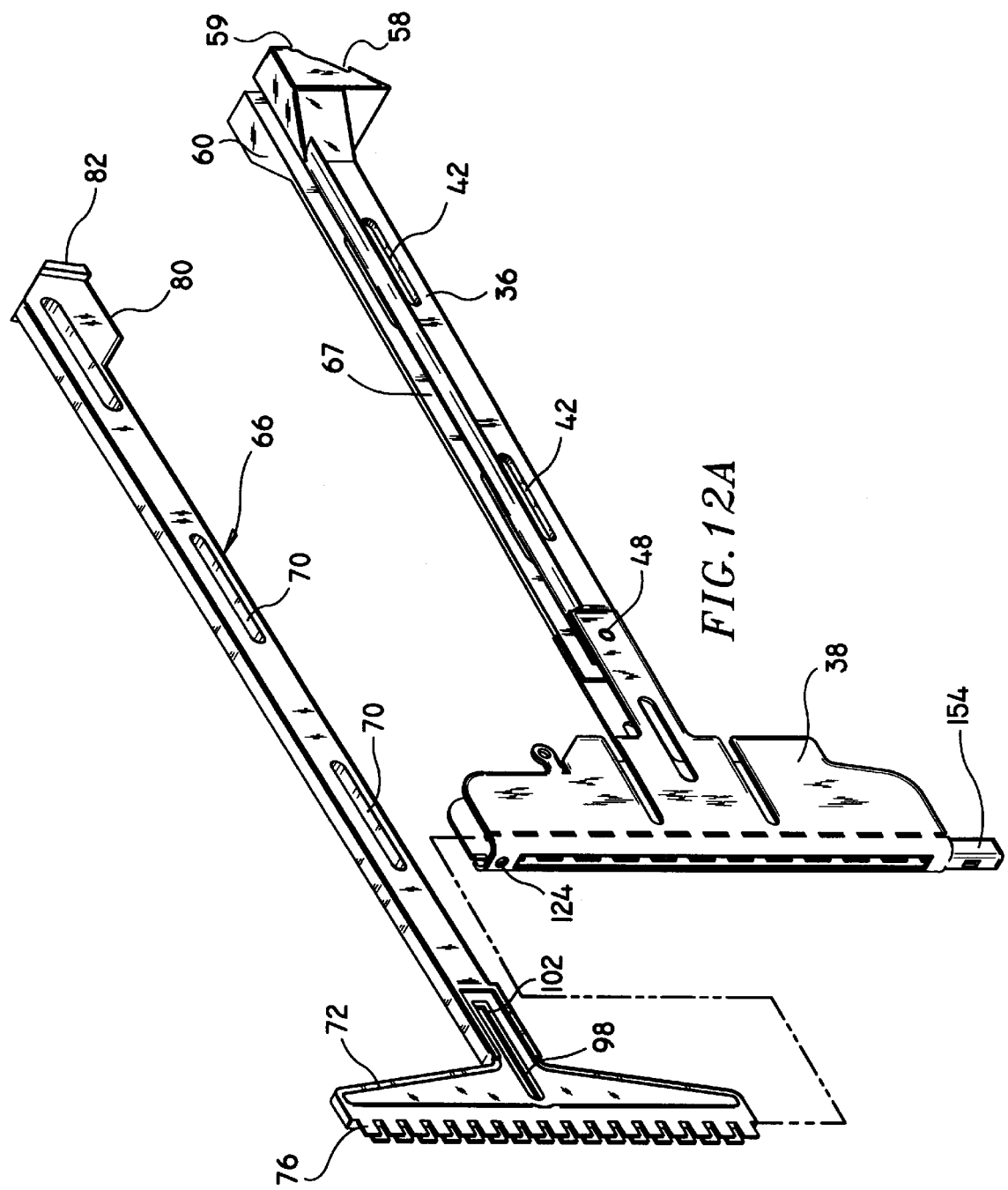

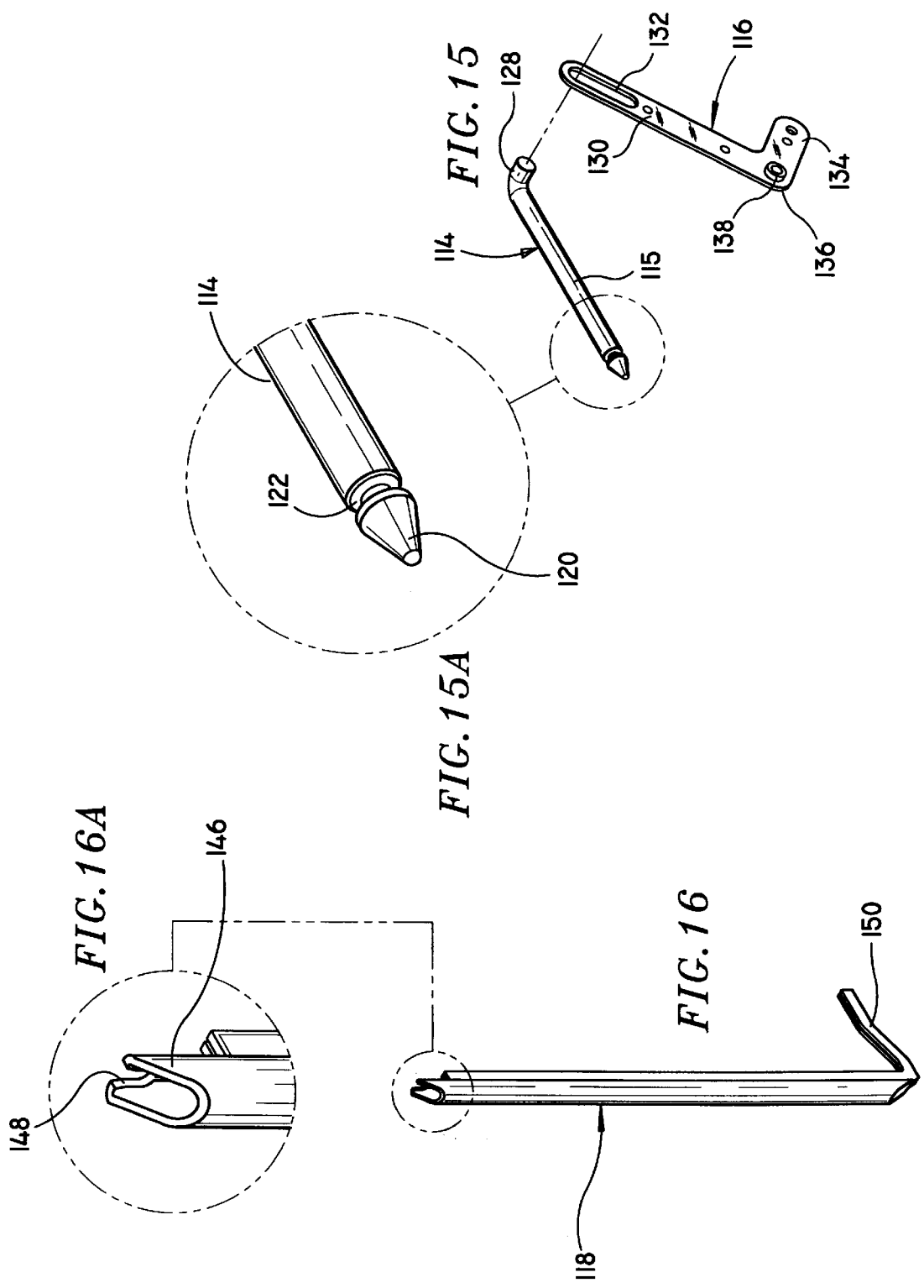

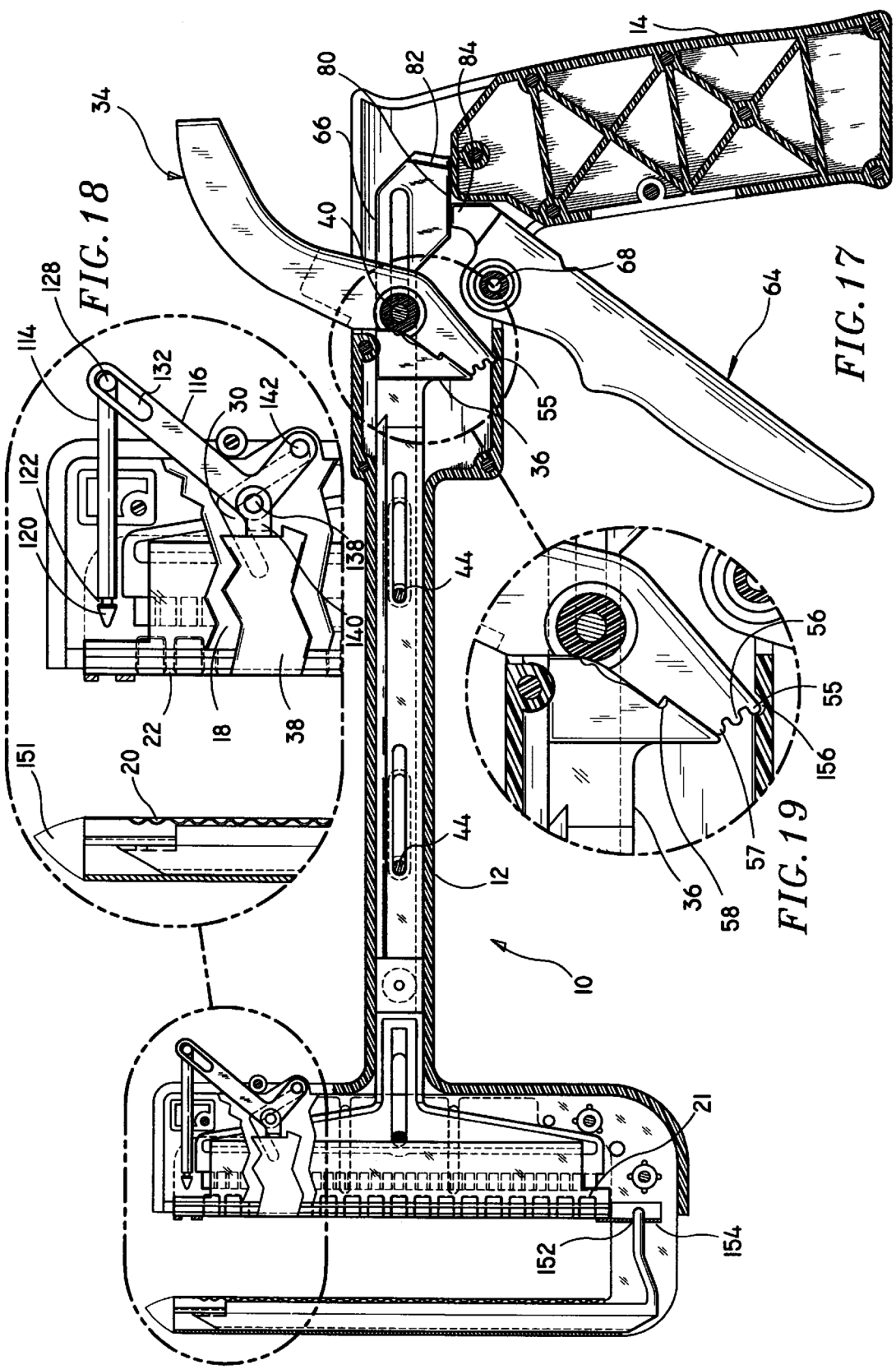

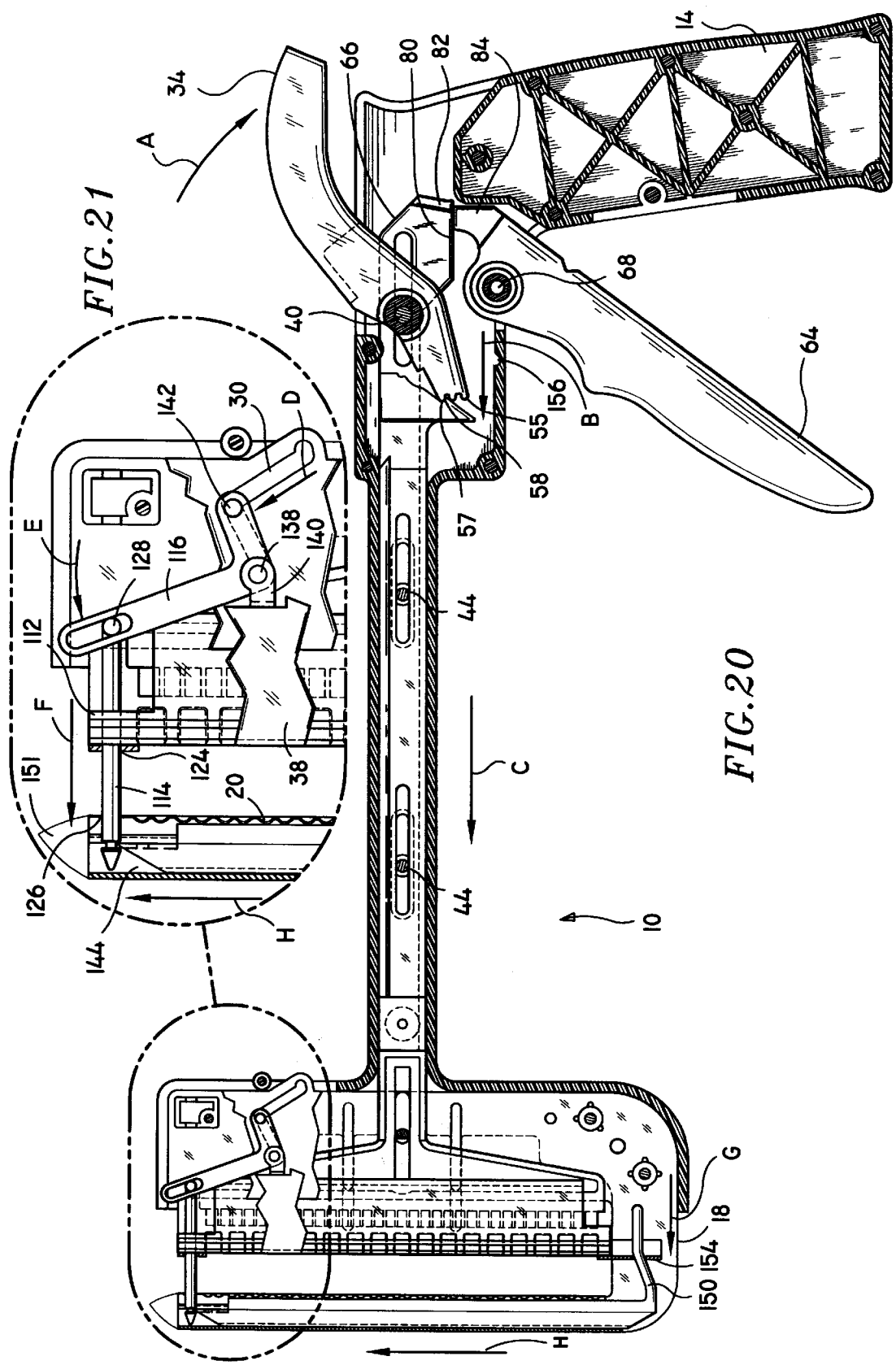

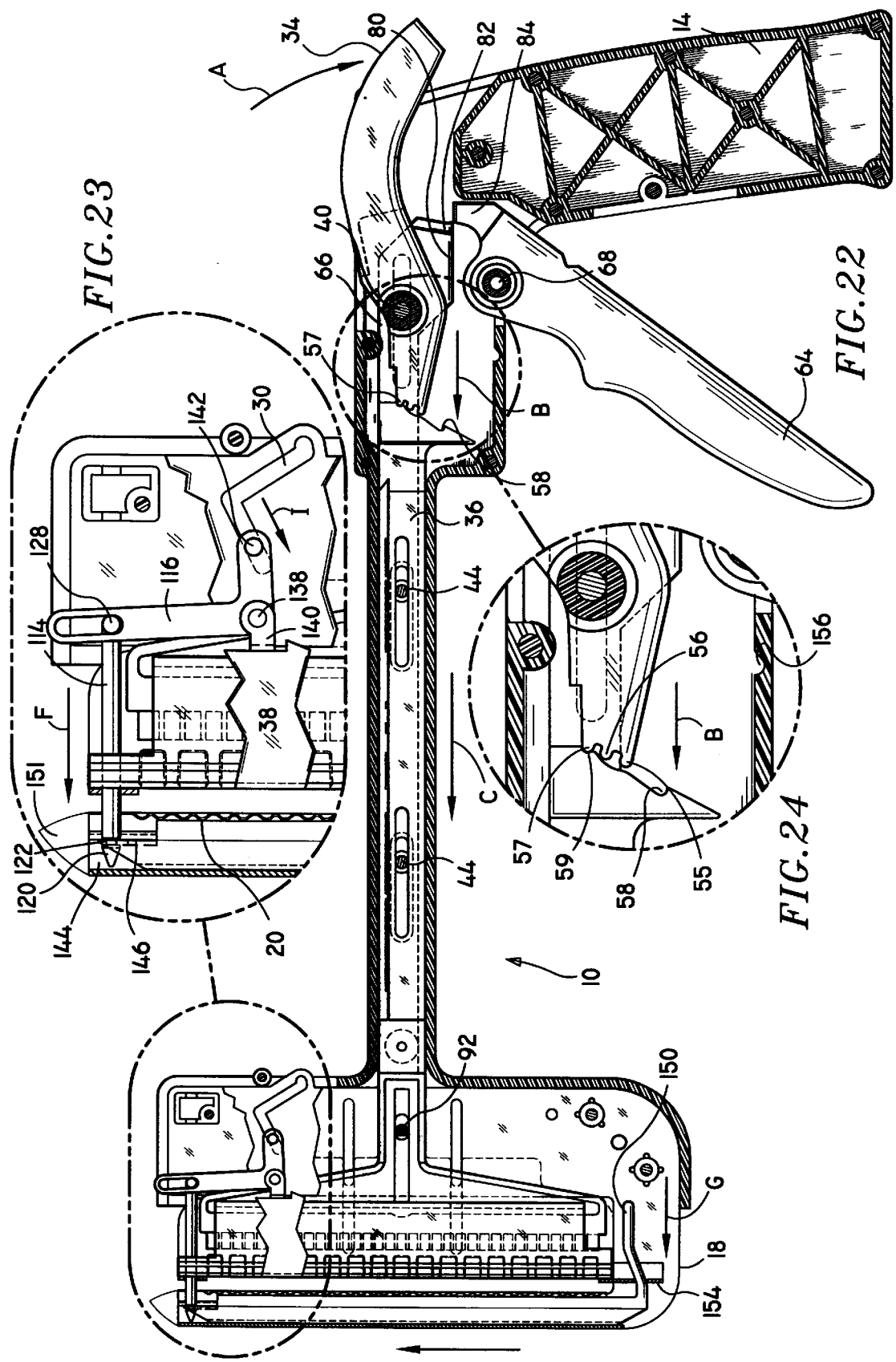

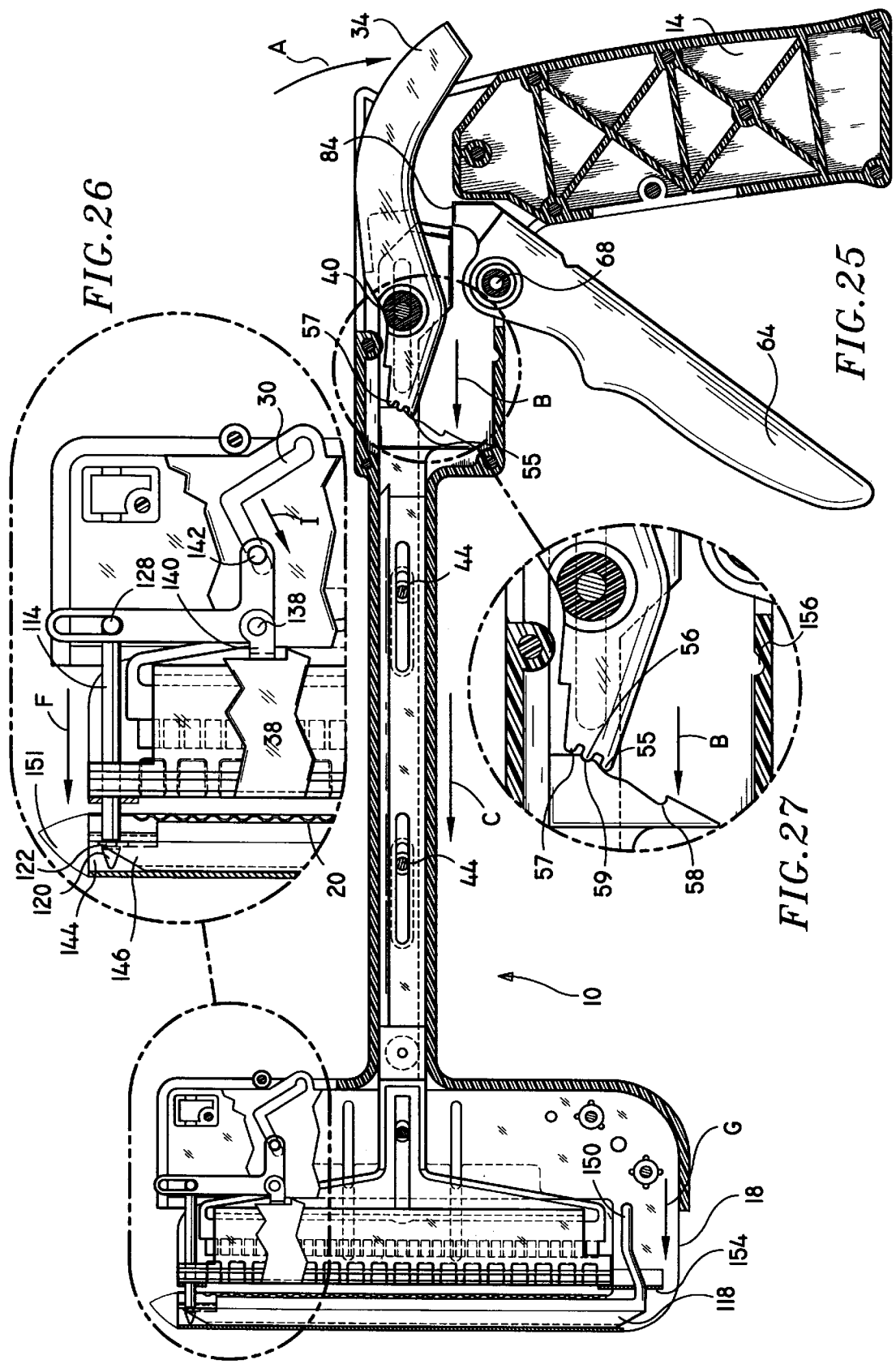

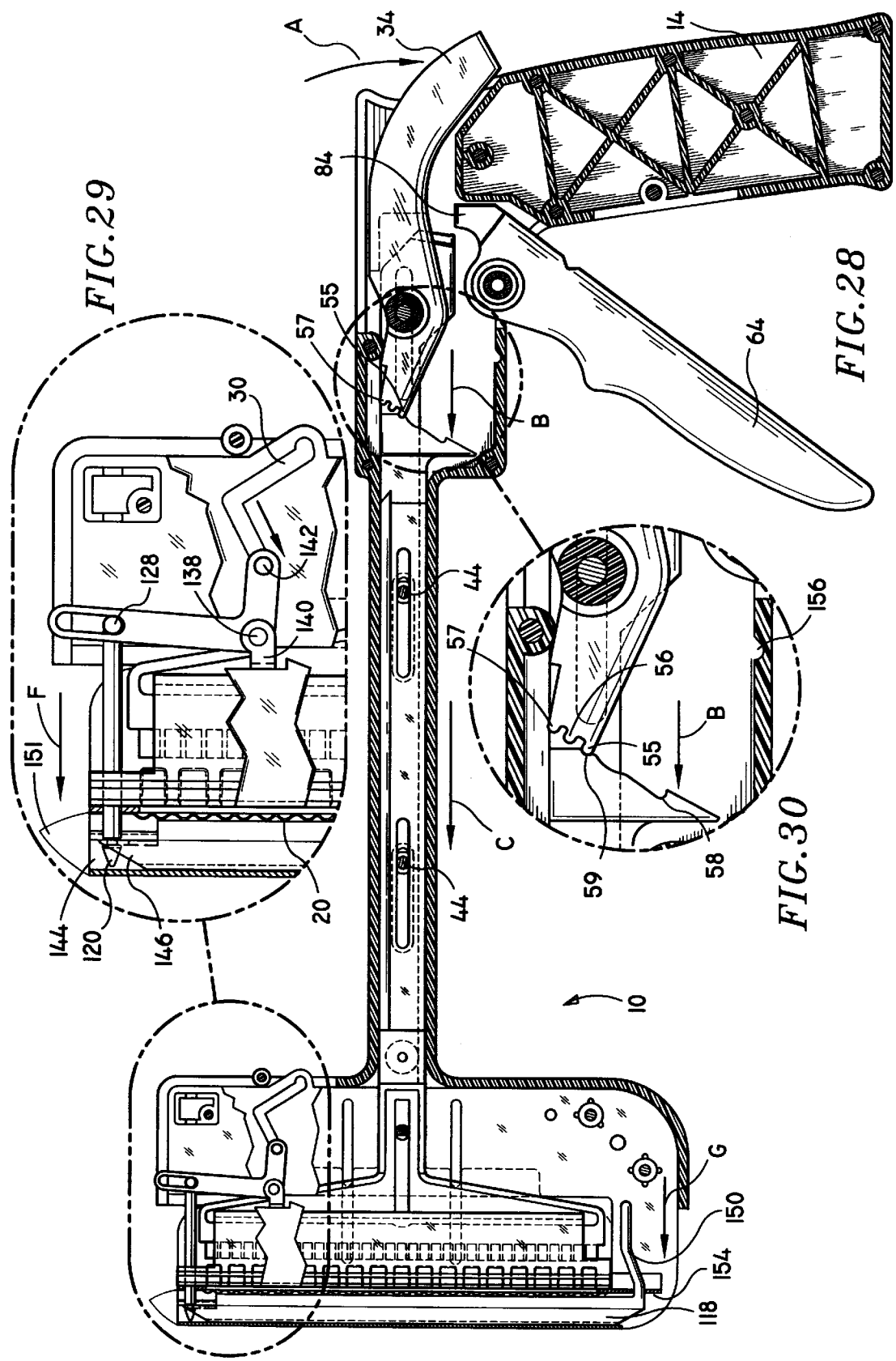

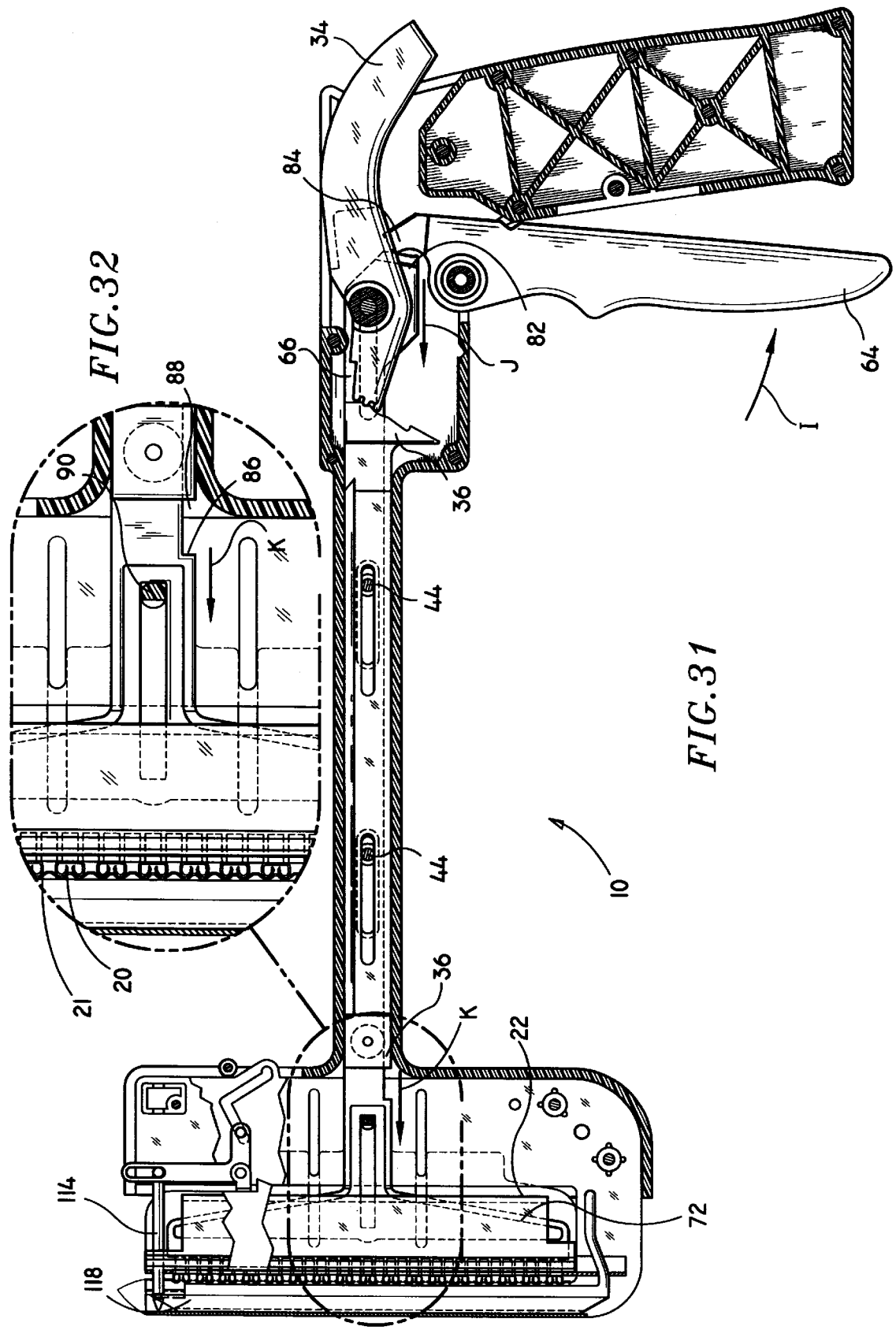

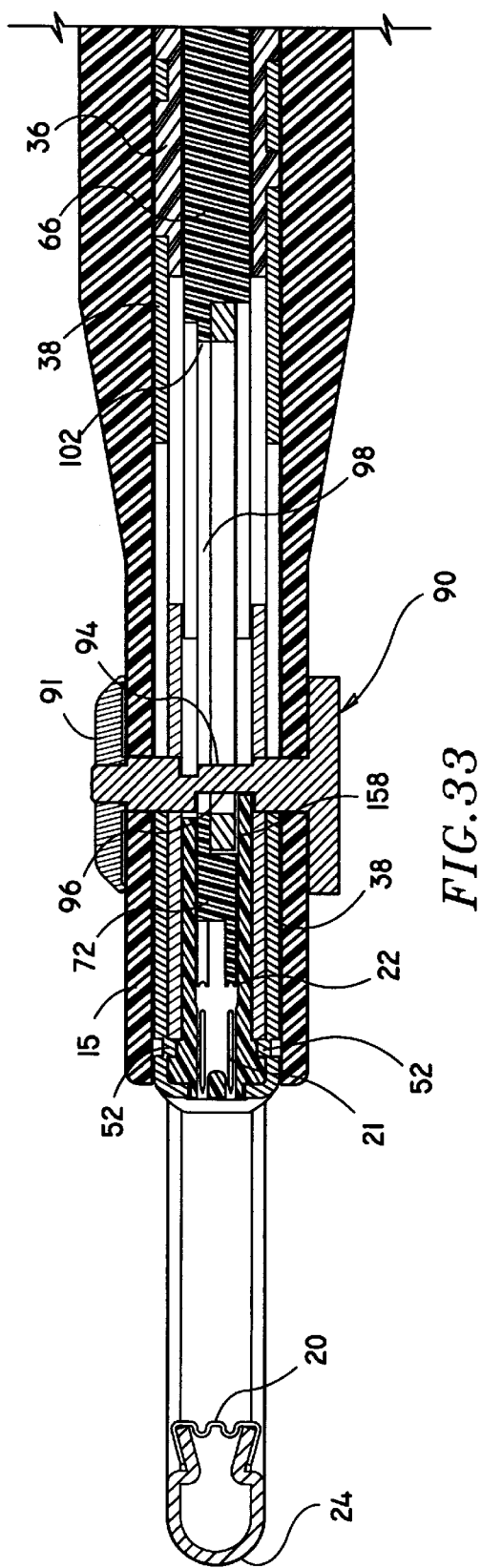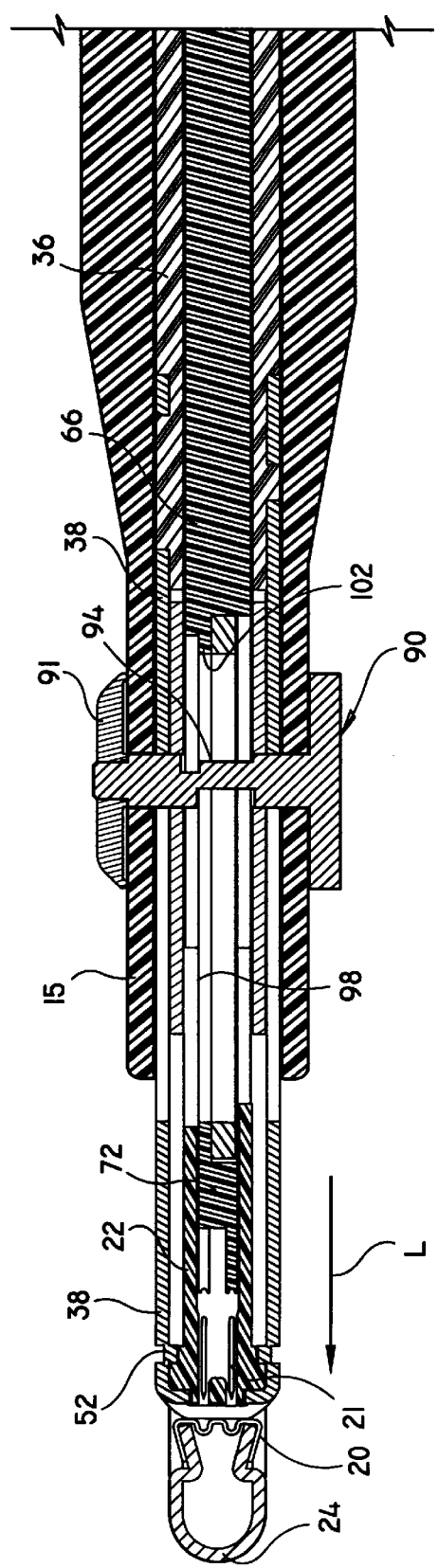

SURGICAL FASTENER APPLYING DEVICE

RELATED APPLICATIONS

This application is a Continuation of U.S. patent application Ser. No. 08/618,436, filed Mar. 15, 1996, now U.S. Pat. No. 5,810,240.

BACKGROUND

1. Technical Field

The present disclosure relates generally to a surgical device. More specifically, the present disclosure relates to a fastener applying device for simultaneously applying an array of fasteners to body tissue.

2. Background of Related Art

Surgical fastening devices for simultaneously applying an array of surgical fasteners, e.g., staples or other types of fasteners are known in the art. Such devices are used for joining body tissue such as, for example, intestinal and gastric walls with spaced parallel rows of longitudinally aligned fasteners. These surgical fastening devices reduce the time of wound closure in a surgical procedure.

Typically, these devices include a fastener holder disposed on one side of the tissue to be joined, and an anvil assembly parallel to the fastener holder on the other side of the tissue to be fastened. The fastener holder is moved linearly towards the anvil assembly so that the tissue is clamped between them. The fasteners are driven from the fastener holder so that the ends of the fasteners pass through the tissue and form finished fasteners as they make contact with the anvil assembly, thereby producing an array of finished fasteners in the tissue. The fasteners can be one or two piece and made of metal, non-absorbable polymers, or bioabsorbable polymers such as plyglycolide, polylactide, and copolymers thereof.

U.S. Pat. No. 5,137,198 to Nobis et al. ("Nobis") discloses a fastener applying device including a cartridge that is advanced towards an anvil assembly by an advancing mechanism. The advancing mechanism includes a first actuator member for advancing the cartridge towards the anvil assembly at an accelerated rate and a second actuator member spaced from the first actuator member for incrementally advancing the cartridge towards the anvil assembly.

One problem associated with such a device is that a surgeon must be able to move between and manipulate the first and second spaced actuator members while simultaneously maintaining the fastener applying device in a substantially fixed position with respect to body tissue to be repaired. This may be difficult to accomplish during the course of a surgical procedure.

Typically, fastener applying devices include a pusher bar that is advanced over a predetermined stroke to interact with and eject the fasteners from the cartridge. At least one driver is positioned within the cartridge between the distal end of the pusher bar and the fasteners such that the pusher bar advances the drivers into engagement with the fasteners. The length of the drivers may be varied to facilitate ejection of different size fasteners from a fastener applying device having a fixed pusher bar stroke.

U.S. Pat. No. 3,692,224 to Astafiev et al. describes a fastener applying device in which the driver is integrally formed with the pusher bar and not housed within the cartridge. The pusher bar is movable over a fixed stroke to eject the fasteners from the cartridge. Because the stroke of the pusher bar is fixed, only a single size fastener can be properly ejected from each fastener applying device. If a cartridge housing fasteners not sized for use with a particular fastener applying device is inserted into the fastener applying device, advancement of the pusher bar over its fixed stroke will result in either overadvancement or underadvancement of the fasteners into body tissue.

Accordingly, a need exists for an improved fastener applying device which overcomes the above-noted disadvantages, is easy to use and provides greater reliability when repairing tissue.

SUMMARY

In accordance with one aspect of the present disclosure, a fastener applying device having a single actuator to perform fast closure and incremental advancement of a cartridge assembly with respect to an anvil assembly is provided. The device includes an approximation mechanism including a pivotable approximating clamp, a longitudinally extending clamp slide, and a cartridge carrier. The cartridge carrier is supported on the distal end of the clamp slide and is adapted to receive a cartridge housing a plurality of fasteners. The clamp slide is restricted to linear movement within the body of the fastener applying device by a series of guide pins. The proximal end of the clamp slide is positioned to engage a distal end of the pivotable clamp as the clamp is pivoted to advance the clamp slide and cartridge carrier towards a distally located anvil assembly.

The distal end of the pivotable clamp includes a plurality of vertically aligned detents which are configured to be releasably received in a pair of vertically aligned recesses formed in the proximal end of the clamp slide. The approximation clamp is pivotable to sequentially move each one of the detents into locking engagement with each of the recesses to define a plurality of different stages of approximation. The engaging surfaces of the approximation clamp and the clamp slide are configured to provide fast closure of the device as the detents are moved into engagement with the bottom recess and incremental closure of the device as the detents are moved into engagement with the upper recess.

The fastener applying device preferably further includes an adjustment mechanism that changes the maximum stroke of the pusher bar to facilitate ejection of different size fasteners from cartridges housing only fasteners, i.e., the drivers are not housed within the cartridge. The adjustment mechanism includes an adjustment member having a shaft having at least two flats formed at different depths into the shaft. The shaft is rotatably supported on the body of the device and extends through an adjustment slot formed in the pusher bar of the fastener applying device. The shaft is movable to align each of the flats with the proximal end of the adjustment slot to limit the effective stroke of the pusher bar. Each flat is formed to facilitate ejection of a particular size fastener from the device. Since each of the flats is formed in the adjustment member to a different depth, the maximum stroke of the pusher bar can be changed by rotating the adjustment shaft to align a different flat with the proximal end of the adjustment slot.

To prevent insertion of a cartridge into a fastener applying device set to receive a cartridge housing different size fasteners, a cartridge housing particular size fasteners, e.g., 4.8 mm fasteners, may include a proximally extending leg. When the adjustment member is properly set to eject the fasteners, the proximally extending leg will be aligned with a recess in the adjustment shaft allowing the cartridge to be inserted into the cartridge carrier. However, if the adjustment shaft is improperly set, i.e., set to eject a different size or smaller fastener, the recess in the adjustment shaft configured to receive the cartridge leg will not be aligned with the leg and the adjustment shaft will obstruct passage of the cartridge into the cartridge carrier.

BRIEF DESCRIPTION OF THE DRAWINGS

Various embodiments are described herein with reference to the drawings wherein:

FIG. 1 is a perspective view of one embodiment of the fastener applying device of the present disclosure;

FIG. 2 is a perspective view of the distal end of the embodiment of the disclosure shown in FIG. 1 with the cartridge assembly in an advanced position;

FIG. 3 is a perspective view with parts separated of the device shown in FIG. 1;

FIG. 8 is a perspective view of the cartridge assembly of the device shown in FIG. 1;

FIG. 9 is a cross-sectional view taken along section line 9—9 of FIG. 8;

FIG. 10 is a perspective view of the pusher bar and proximal portion of the clamp slide of the device shown in FIG. 1;

FIG. 11 is an enlarged view of the proximal end of the pusher bar and clamp slide as shown in FIG. 10;

FIG. 12 is a perspective view with parts separated of the pusher bar, the proximal portion of the clamp slide, and the metal support member of the pusher bar of the device shown in FIG. 1;

FIG. 12A is a perspective view with parts separated of the clamp slide and the pusher bar of the device shown in FIG. 1;

FIG. 13 is an enlarged view of the indicated area of detail shown in FIG. 12;

FIG. 15 is a perspective view of a portion of the alignment mechanism of the device shown in FIG. 1;

FIG. 15A is an enlarged view of the indicated area of detail shown in FIG. 15;

FIG. 16 is a perspective view of the lateral slide element of the alignment mechanism of the device shown in FIG. 1;

FIG. 16A is an enlarged view of the indicated area of detail of FIG. 16;

FIG. 17 is a side cross-sectional view of the device shown in FIG. 1 with the clamp slide in a retracted position;

FIG. 18 is an enlarged view of the indicated area of detail shown in FIG. 17;

FIG. 19 is an enlarged view of the indicated area of detail shown in FIG. 17;

FIG. 20 is a side cross-sectional view of the device shown in FIG. 1 at a first stage of approximation and prior to firing the fasteners;

FIG. 21 is an enlarged view of the indicated area of detail of FIG. 20;

FIG. 22 is a side cross-sectional view of the device shown in FIG. 1 at a second stage of approximation;

FIG. 23 is an enlarged view of the indicated area of detail of FIG. 22;

FIG. 24 is an enlarged view of the indicated area of detail of FIG. 22;

FIG. 25 is a side cross-sectional view of the device shown in FIG. 1 at a third stage of approximation and prior to firing the fasteners;

FIG. 26 is an enlarged view of the indicated area of detail of FIG. 25;

FIG. 27 is an enlarged view of the indicated area of detail of FIG. 25;

FIG. 28 is a side cross-sectional view of the device shown in FIG. 1 at a fourth stage of approximation and prior to firing of the fasteners;

FIG. 29 is an enlarged view of the indicated area of detail of FIG. 28;

FIG. 30 is an enlarged view of the indicated area of detail of FIG. 28;

FIG. 31 is a side cross-sectional view of the device shown in FIG. 1 at the third stage of approximation in a fully actuated condition;

FIG. 32 is an enlarged view of the indicated area of detail of FIG. 31;

FIG. 33 is a top cross-sectional view of the distal end of the device shown in FIG. 1 with the clamp slide in a retracted position;

FIG. 34 is a top cross-sectional view of the distal end of the device shown in FIG. 1 with the cartridge and anvil assemblies at a fourth stage of approximation;

DETAILED DESCRIPTION OF THE PREFERRED EMBODIMENTS

Figure 5:
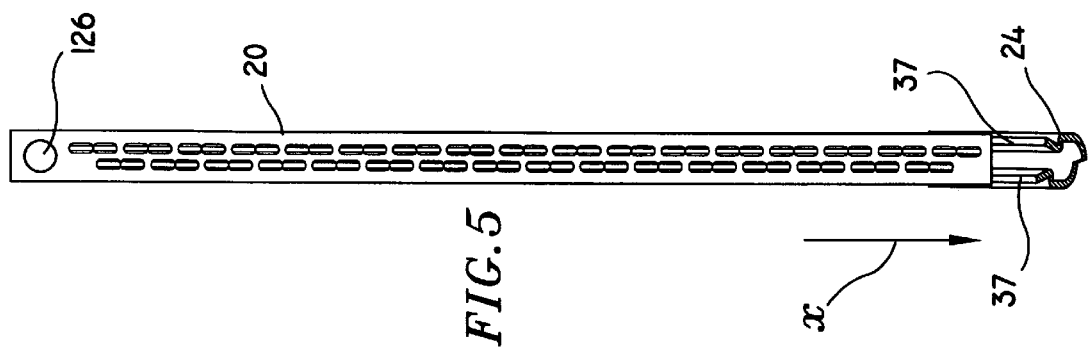
FIG. 5 is a front elevational view of the anvil of the device shown in FIG. 1.

Preferred embodiments of the presently disclosed fastener applying device will now be described in detail with reference to the drawings, in which like reference numerals designate identical or corresponding elements in each of the several views.

Referring to the drawings, FIGS. 1 and 2 illustrate a first embodiment of the fastener applying device shown generally as 10. Fastener applying device 10 includes a housing 12 including stationary handle 14, a distally extending body portion 16, and a transverse body portion 15. Transverse body portion 15 is configured to receive support frame 18. Housing 12 may be constructed from plastic material in the form of molded housing half-sections 12a and 12b. Preferably, housing 12 is constructed from fiberglass reinforced plastic, although other materials having the requisite strength requirements may be used.

FIG. 3 illustrates a perspective view of fastener applying device 10 with the internal components of device 10 separated from each other. The device 10 may be is fastened together using screws 19 that extend between housing half-sections 12a and 12b, although adhesives, ultrasonic welding, and other known fastening methods may also be used to fasten the components of the device together.

Figure 4:
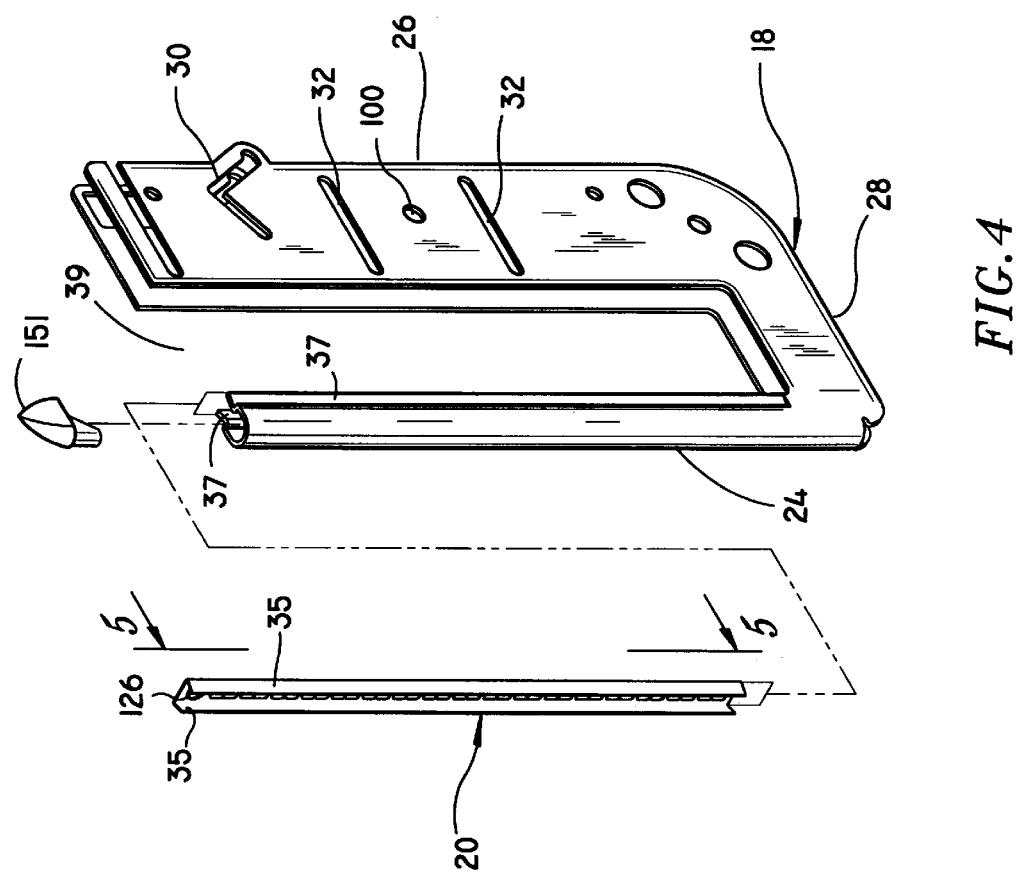
FIG. 4 is a perspective view with parts separated of a portion of the distal end of the device shown in FIG. 1.

Referring to FIGS. 4 and 5, an anvil 20 is fastened to a first leg 24 of the support frame 18. Any known fastening technique may be used to fasten the anvil 20 to first leg 24. Preferably, anvil 20 includes a pair of inwardly converging legs 35 dimensioned to be received on a pair of outwardly diverging legs 37 formed on first leg 24. During manufacturing of device 10, anvil 20 may be slid onto first leg 24, in the direction as indicated by arrow "X", and secured in position via any known means, e.g., welding, crimping, etc. The anvil 20 may be constructed from any material having the requisite strength requirements, but is preferably formed from cold rolled steel.

The support frame 18 is substantially U-shaped and includes first leg 24, a second leg 26, and a base portion 28. First leg 24 extends substantially parallel to second leg 26. Second leg 26 is formed with a cam slot 30 and a pair of elongated guide nubs 32, which will be discussed in further detail below. Base portion 28 extends between first and second legs 24 and 26 to define a space 39. The support frame 18 may be monolithically formed by bending a sheet of material into the desired shape. Preferably, support frame 18 is constructed from stainless steel, although other materials having the requisite strength requirements may be used.

Figure 6:
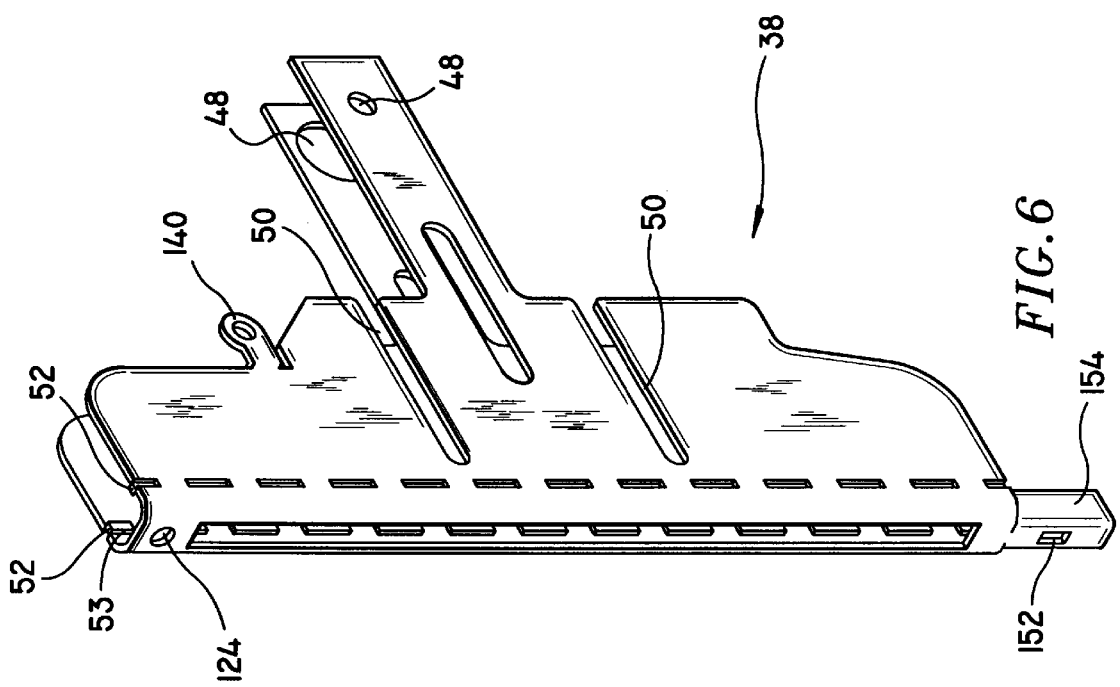
FIG. 6 is a perspective view of the cartridge carrier of the device shown in FIG. 1.
Figure 7:
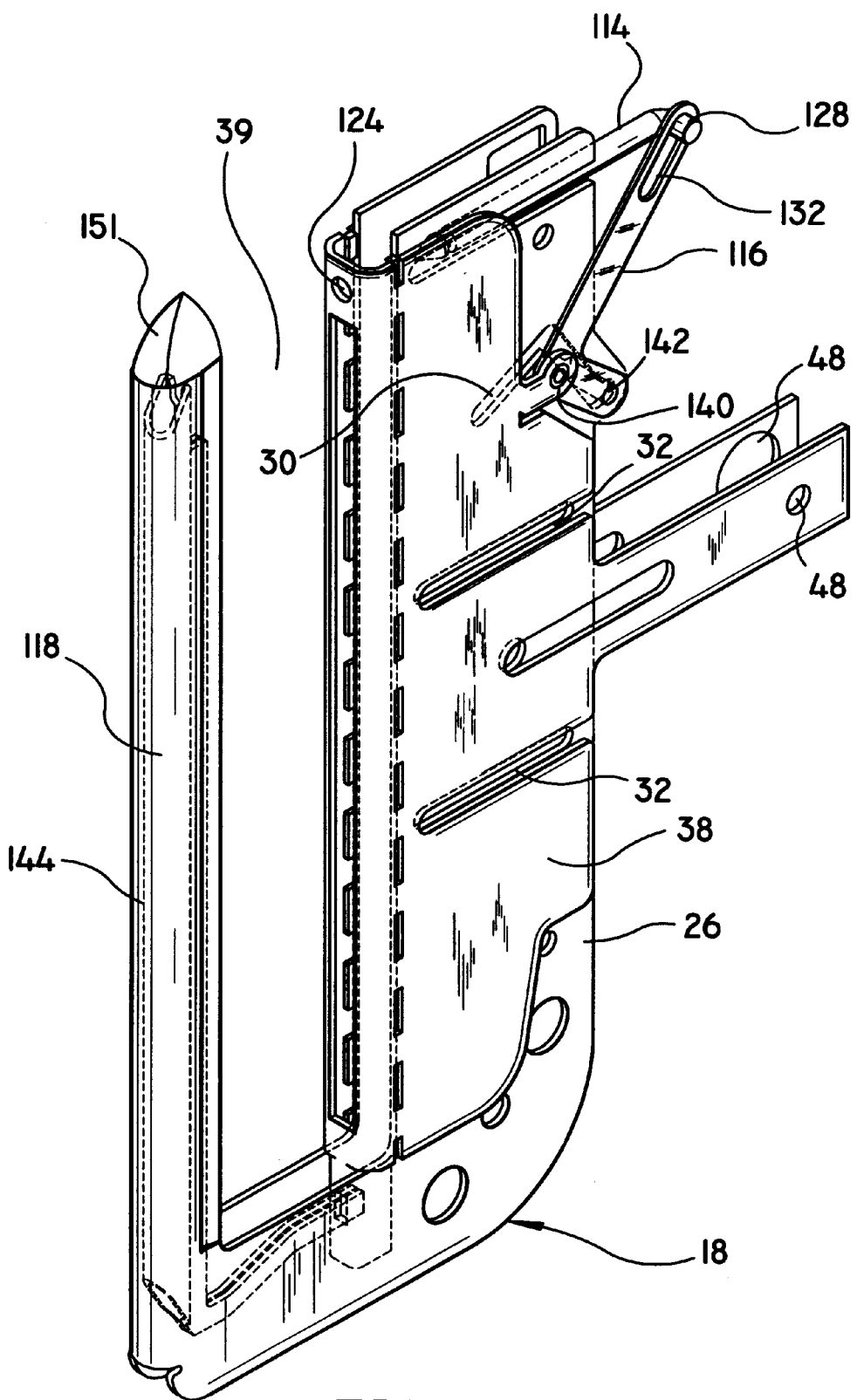
FIG. 7 is a perspective view of a portion of the distal end of the device shown in FIG. 1.

Referring to FIGS. 6 and 7, cartridge carrier 38 is slidably supported about second leg 26 of support frame 18 and is movable through the space 39 towards first leg 24. Elongated slots 50 extend through cartridge carrier 38 and are configured to receive the guide nubs 32 formed on the second leg 26. The guide nubs 32 define a linear path of travel for the cartridge carrier 38 as it advances between the first and second legs 24 and 26 of support frame 18.

FIGS. 3, 8 and 9 illustrate cartridge assembly 22. Cartridge assembly 22 includes a body 104 having a distal face 106 which is spaced from an open proximal end 74. A pusher bar channel 108 extends from the open end 74 through a portion of body 104. A plurality of slots 110 house fasteners 21 (FIG. 3) and are configured to receive distally extending fingers 76 of pusher bar 66. The slots 110 extend between the distal end of pusher bar channel 108 and the distal face 106 of cartridge assembly 22. The outer surface of cartridge body 104 includes a pair of transversely extending flanges 54.

Referring temporarily back to FIG. 6, cartridge carrier 38 is provided with inwardly extending projections 52 which define a channel 53 configured to receive cartridge assembly 22 (FIG. 8). The cartridge assembly 22 can be slid into channel 53 such that projections 52 engage flanges 54 to retain cartridge assembly 22 within cartridge carrier 38. The open end 74 of cartridge body 104 faces the proximal end of the device 10. When the cartridge assembly 22 is properly positioned within channel 53, an opening 124 formed in cartridge carrier 38 is aligned with an opening 112 formed in cartridge assembly 22.

Referring to FIGS. 3 and 10–12A, the fastener applying device 10 has an approximation mechanism for advancing cartridge assembly 22 and cartridge carrier 38. An approximating clamp 34 or lever is pivotably mounted about pivot member 40 which is supported between housing half sections 12a and 12b in the proximal end of housing 12. The approximating clamp 34 is movable into engagement with a proximal end of clamp slide 36 to linearly advance the clamp slide 36 within body portion 16. A plurality of longitudinal slots 42 formed in clamp slide 36 are configured to receive guide pins 44 to limit clamp slide 36 to a linear path of travel.

Referring specifically to FIGS. 12 and 12A, the distal end of clamp slide 36 includes a pair of projections 46. The projections 46 are fastened within a pair of openings 48 formed in a proximal end of cartridge carrier 38, such that linear movement of clamp slide 36 is translated to corresponding linear movement of cartridge carrier 38.

Referring to FIGS. 3, 10 and 11, approximating clamp 34 includes an abutment end 62 having a series of detents 55–57 which are configured to be received in recesses 58 and 59 formed in an angled proximal end 60 of clamp slide 36. The angled proximal end 60 of the clamp slide 36 and the abutment end 62 of the approximating clamp 34 (FIG. 3) are movable into engagement to advance the cartridge assembly 22 towards the anvil 20. Preferably, approximating clamp 34 and clamp slide 36 are constructed of plastic and cartridge carrier 38 is constructed of stainless steel. However, other materials meeting the requisite strength requirements and being suitable for surgical use may be used to construct each of the components of device 10.

FIGS. 3, 12 and 13 illustrate the firing mechanism for applying the fasteners of device 10. The firing mechanism includes a trigger actuator 64 and an elongate pusher bar 66 slidably received in channel 67 formed in clamp slide 36. Trigger actuator 64 is pivotable about pivot pin 68 into engagement with a proximal end of pusher bar 66 to advance pusher bar 66 with respect to cartridge carrier 38. Pivot pin 68 is supported between housing half-sections 12a and 12b.

Pusher bar 66 includes a series of longitudinal slots 70. The slots 70 slidably receive the guide pins 44. Guide pins 44 limit pusher bar 66 to a linear path of travel identical to that of clamp slide 36.

The distal end of pusher bar 66 is formed with a head portion 72 configured to move through the open proximal end 74 of cartridge assembly 22 (FIG. 9) to effect ejection of fasteners 21. A plurality of distally extending fingers 76 are integrally formed on head portion 72. Each finger 76 has a concave distal surface 78 configured to engage the fasteners 21 housed within cartridge assembly 22. Fingers 76 extend from head portion 72 in a pattern that corresponds to the pattern that fasteners 21 are housed within cartridge assembly 22. For example, the pattern may be two staggered rows. Other patterns are also contemplated.

A recess 71 is formed in one side of head portion 72. A metal plate 73 is positioned in recess 71 to provide additional strength to the distal end of pusher bar 66. Due to the increase in strength provided by metal plate 73, pusher bar 66 may be constructed from plastic and still retain the strength to effect ejection of fasteners 21 from fastener applying device 10.

Pusher bar 66 has a ledge 86 located proximally of head portion 72. Ledge 86 is positioned to engage a distal edge 88 formed on clamp slide 36, such that distal movement of clamp slide 36 effects corresponding distal movement of pusher bar 66. Pusher bar 66 remains free to advance distally independently of clamp slide 36 since ledge 86 will be disengaged from distal edge 88 when pusher bar 66 is advanced distally.

As illustrated in FIG. 3, the proximal end of pusher bar 66 has a locking surface 80 and a contact surface 82. The trigger actuator 64 includes an engagement surface 84 which pivots into engagement with contact surface 82 of the pusher bar 66 to advance the pusher bar 66 distally.

Referring temporarily ahead to FIGS. 17–21, when the pusher bar 66 is in a retracted position, locking surface 80 of the pusher bar 66 is positioned to prevent engagement between engagement surface 84 of the trigger actuator 64 and contact surface 82 of pusher bar 66. Thus, locking surface 80 prevents firing fasteners 21 prior to sufficient approximation of cartridge assembly 22 and anvil 20. Before trigger actuator 64 can be rotated counter-clockwise, as viewed in FIG. 21, to eject fasteners 21 from device 10, the approximating clamp 34 must be rotated clockwise from the position of FIG. 17, toward the stationary handle 14 in the direction indicated by arrow "A", to advance clamp slide 36 distally, such that distal edge 88 of clamp slide 36 engages and advances distal ledge 86 of pusher bar 66, to move locking surface 80 distally past engagement surface 84. This frees trigger actuator 64 for pivotal movement to fire the fasteners.

Figure 14:
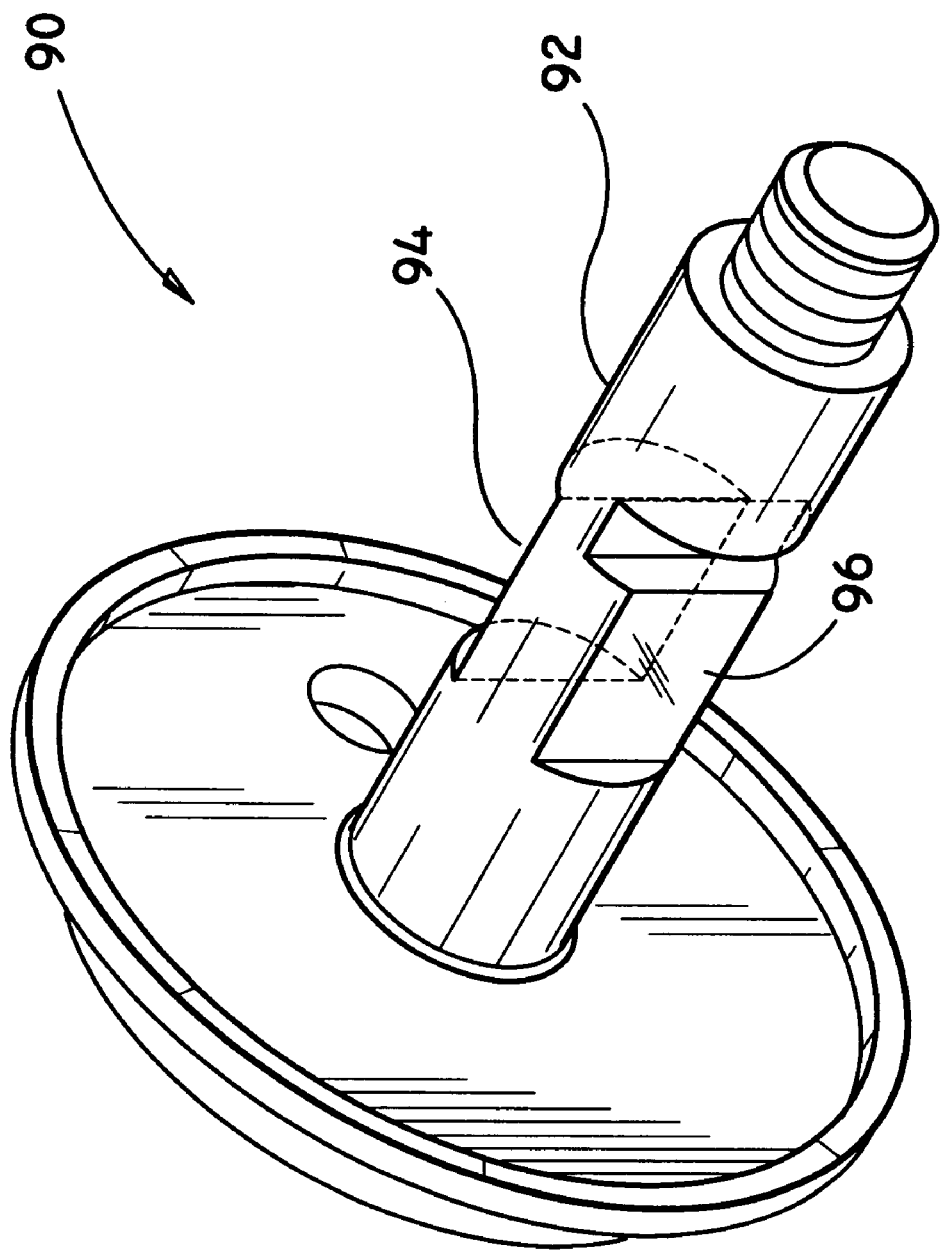
FIG. 14 is a perspective view of the set pin of the adjustment mechanism of the device shown in FIG. 1.

Referring now to FIGS. 3 and 14, an adjustment member 90 is provided in the distal end of the device 10 to facilitate ejection of different size fasteners 21 from fastener applying device 10. Adjustment member 90 includes a cylindrical shaft 92 having a pair of diametrically opposed first and second flats 94 and 96, respectively. Cylindrical shaft 92 extends through an opening 100 (FIG. 4) formed in the second leg 26 of support member 18 and through the distal end of a longitudinal adjustment slot 98 formed in pusher bar 66. The adjustment member 90 is secured to support member 18 by adjustment nut 91. Shaft 92 is rotatable to align one of the opposed flats 94 or 96 with a proximal end 102 of adjustment slot 98 to define a stop surface for the pusher bar 66. See FIG. 12A. Since the flats 94 and 96 are formed at different depths into the cylindrical shaft 92, shaft 92 may be rotated to change the position of the stop surface to vary the stroke of the pusher bar 66.

Referring now to FIGS. 4, 7, and 15–16, an alignment mechanism is operably connected to the approximation mechanism to maintain alignment between cartridge assembly 22 and anvil 20 during approximation of anvil 20 and cartridge 22. The alignment mechanism preferably includes alignment pin 114, L-shaped link 116, and slide element 118.

Alignment pin 114 includes a cylindrical shaft 115 having a distal tapered nose 120 and an annular groove 122 located proximally of nose 120. The pin 114 is configured to pass through an opening 112 (FIG. 8) formed in cartridge assembly 122, opening 124 formed in cartridge carrier 38, and opening 126 formed in anvil 20. The proximal end of pin 114 includes an angled portion 128 which is operably connected to the L-shaped link 116.

L-shaped link 116 includes a first leg 130 having an elongated slot 132, a second leg 134 adapted to receive a camming pin 142 (FIG. 15), and a central portion 136 having a pivot member 138 configured to pivotably engage connector 140. The connector 140 is integrally formed with cartridge carrier 38. Elongated slot 132 is dimensioned to slidably receive angled portion 128 of alignment pin 114, and camming pin 142 is positioned in cam slot 30 formed in support member 18.

Slide element 118 is slidably received in channel 144 formed in first leg 24 of support member 18 (FIG. 7) and includes a forked tip 146 at one end having a recess 148 configured to be received in annular groove 122 of alignment pin 114 (FIG. 15A). Longitudinal extension 150 extends from the other end of slide element 118 and is dimensioned to be received within opening 152 (FIG. 6) in extension 154 formed on cartridge carrier 38. A cover 151 is fitted in the open end of channel 144 (FIG. 7).

Referring now to FIGS. 17–30, operation of the fastener applying device 10 will now be described. FIGS. 17–19 illustrate fastener applying device 10 in a retracted position prior to actuation of device 10. Approximating clamp 34 is in its pre-actuated position. Bottom detent 55 on approximating clamp 34 engages recess 156 formed in housing 12 of device 10 to releasably retain the approximating clamp 34 in the pre-actuated position. Clamp slide 36 and pusher bar 66 are fully retracted such that locking surface 80 formed at the distal end of pusher bar 66 is positioned to prevent rotation of trigger actuator 64, thereby preventing firing of fastener applying device 10 before the cartridge assembly 22 and the anvil 20 have been approximated to within a predetermined distance of each other.

FIGS. 20 and 21 illustrate fastener applying device 10 at a first stage of approximation. Approximating clamp 34 has been pivoted clockwise, as indicated by arrow "A", to disengage detent 55 from recess 156 and to move detent 57 into engagement with bottom recess 58 formed in the proximal end of clamp slide 36. Engagement between the distal end of approximating clamp 34 and clamp slide 36 causes clamp slide 36 to move distally, as indicated by arrow "B", and results in corresponding distal movement of cartridge carrier 38 and pusher bar 66 as indicated by arrow "C". (Pusher bar 66 is advanced distally with clamp slide 36 due to engagement between distal edge 88 of clamp slide 36 and ledge 86 formed on pusher bar 66. See FIG. 12.) At this stage of approximation, locking surface 80 remains in position, i.e., in abutment with engagement surface 84, to prevent rotation of trigger actuator 64 and to prevent firing of fastener applying device 10.

As best shown in FIG. 21, L-shaped link 116 of the alignment mechanism is pivotally connected to connector 140, which extends from cartridge carrier 38, by pivot member 138. As L-shaped link 116 is moved distally by cartridge carrier 38, camming pin 142 is moved within cam slot 30, as indicated by arrow "D", to rotate L-shaped link 116 counter-clockwise about pivot member 138, as indicated by arrow "E", and advance alignment pin 114 distally, as indicated by arrow "F", through openings 124 and 126 formed in cartridge carrier 38 and anvil 20 into channel 144 in support frame 18. Distal movement of cartridge carrier 38 also causes extension 154 formed on the cartridge carrier 38 to move distally, as indicated by arrow "G", into engagement with longitudinal extension 150 extending from slide element 118. Engagement between extension 154 and longitudinal extension 150 moves slide element 118 upwardly through channel 144 in support frame 18, as indicated by arrow "H", towards alignment pin 114.

FIGS. 22–24 illustrate fastener applying device 10 at a second stage of approximation. Approximating clamp 34 has been pivoted further clockwise, as indicated by arrow "A", to move detent 57 from engagement with bottom recess 58 in the proximal end of clamp slide 36 to engagement with top recess 59 in the proximal end of clamp slide 36. Clamp slide 36 has been moved distally, as indicated by arrow "B", resulting in corresponding movement of cartridge carrier 38 and pusher bar 66, as indicated by arrow "C". Locking surface 80 of pusher bar 66 has been moved distally of engagement surface 84 of trigger actuator 64 to permit rotation of trigger actuator 64 about pivot member 68 to enable firing of fastener applying device 10, if desired.

As illustrated in FIG. 23, the orientation of cam slot 30 changes to redirect movement of camming pin 142 after device 10 advances past the first stage of approximation. Movement of the camming pin 142 through cam slot 30, as indicated by arrow "I", rotates L-shaped link 116 clockwise as cartridge carrier 38 is moved distally. Distal movement of cartridge carrier 38 and clockwise rotation of L-shaped link 116 have the combined effect of maintaining alignment pin 114 in a substantially fixed position within channel 144 in support frame 18. As shown in FIG. 22, distal movement of extension 154 causes slide element 118 to move upwardly through channel 144 such that forked tip 146 of slide element 118 engages with annular channel 122 formed in alignment pin 114.

FIGS. 25–27 illustrate fastener applying device 10 at a third stage of approximation. Approximating clamp 34 has been pivoted further clockwise about pivot member 40, as indicated by arrow "A", to disengage detent 57 from engagement with top recess 59 and to move middle detent 56 into engagement with top recess 59. Clamp slide 36 has been moved distally, as indicated by arrow "B", resulting in corresponding distal movement of cartridge carrier 38, as indicated by arrow "G", and pusher bar 66, as indicated by arrow "C". Locking surface 80 of pusher bar 66, being moved further distally, continues to permit rotation of trigger actuator 64 about pivot member 68 to enable firing of fastener applying device 10.

As illustrated in FIG. 26, camming pin 142 of the alignment mechanism has been moved further towards the distal end of cam slot 30, as indicated by arrow "I", to rotate L-shaped link clockwise. Movement of the cartridge carrier 38 distally, which moves alignment pin 114 distally, and clockwise rotation of L-shaped link 116, which moves alignment pin 114 proximally, has the combined effect of maintaining alignment pin 114 in a substantially fixed position within channel 144 in support frame 118. Because of the shape of longitudinal extension 150, forked tip 146 of slide element 118 remains in substantially the same position within channel 144 engaged with annular channel 122 of alignment pin 114. See FIG. 25.

FIGS. 28–30 illustrate fastener applying device 10 in the fourth stage of approximation. Approximating clamp 34 has been pivoted about pivot member 40 to its clockwise-most position, disengaging detent 56 from top recess 59 and moving bottom detent 55 into engagement with top recess 59. Clamp slide 36, has been moved distally, as indicated by arrow "B", resulting in corresponding distal movement of cartridge carrier 38 and pusher bar 66, as indicated by arrows "G" and "C", respectively. Locking surface 80 of pusher bar 66 remains out of engagement with surface 84 of trigger actuator 64.

Camming pin 142 has been moved to the distal end of cam slot 30 to effect clockwise rotation of L-shaped link 116. Movement of cartridge carrier 38 distally combined with clockwise rotation of L-shaped link 116 has the effect of maintaining the alignment pin 114 in a substantially stationary position within channel 144 in support frame 18. Because of the shape of longitudinal extension 150, forked tip 146 of slide element 118 remains in substantially the same position within channel 144 engaged with annular channel 122 of alignment pin 114.

As described, fastener applying device 10 may be fired from any one of the second, third or fourth stages of approximation. Each of these stages is within the zone of fire of device 10. By providing different stages of approximation within the zone of fire, the device 10 may be approximated to take into account different body tissue thicknesses. Although device 10 is disclosed as having four stages of approximation, a fewer or a greater number of stages is also contemplated.

FIGS. 31 and 32 illustrate fastener applying device 10 in the third stage of approximation within the zone of fire by way of example. Trigger actuator 64 has been rotated in a counter-clockwise direction about pivot member 68, as indicated by arrow "I", to move engagement surface 84 into abutment with contact surface 82 to advance pusher bar 66, as indicated by arrow "J". Head portion 72 of pusher bar 66 has been advanced distally, as indicated by arrow "K", to eject fasteners 21 from cartridge assembly 22 against anvil 20. As illustrated in FIG. 32, distal movement of pusher bar 66 causes pusher bar ledge 86 to move away from distal edge 88 of clamp slide 36.

When fastener applying device 10 has been approximated to within the zone of fire, alignment pin 114 and slide element 118 are engaged to form a box configuration with support frame 18. The box configuration provides lateral and longitudinal stability and alignment at the distal end of device 10. Because of the increased stability provided by the alignment mechanism, metal support frame 18 need not extend proximally within the housing 12 of the device 10, as is common in conventional fastener applying devices but may be supported between molded housing half-sections 12a and 12b.

Figure 35:
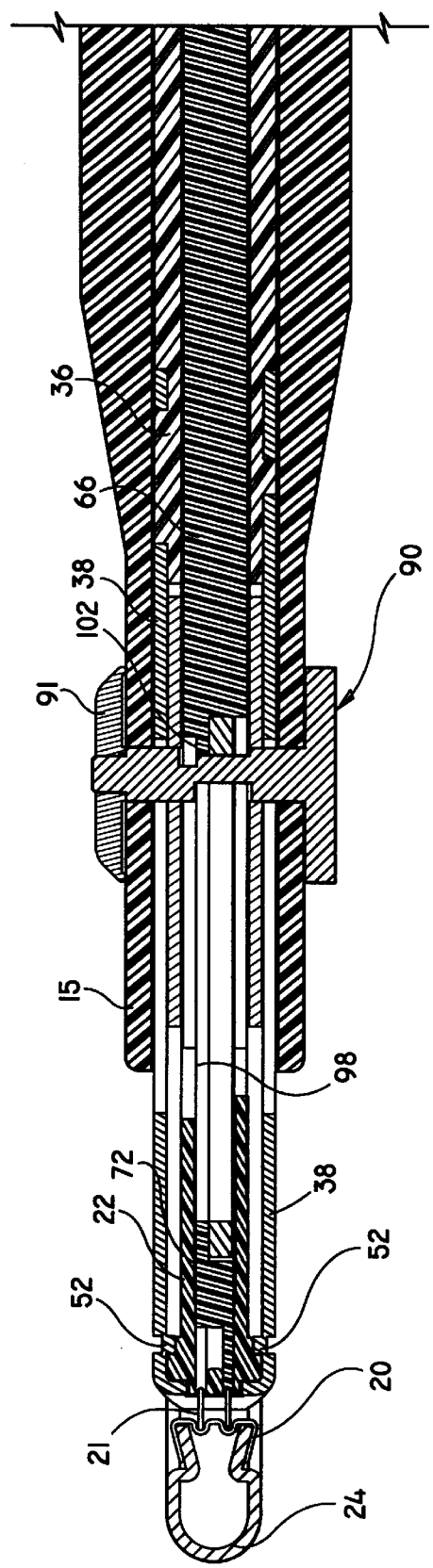
FIG. 35 is a top cross-sectional view of the distal end of the device shown in FIG. 1 with the pusher bar in an advanced position.

FIGS. 33–35 illustrate a top cross-section of the distal end of device 10 as device 10 is moved sequentially from a retracted position, to a fully approximated position, to a fired position. In FIG. 33, cartridge 22 is retained in cartridge carrier 38 by projections 52. Cartridge carrier 38 is spaced from anvil 20 within transverse body portion 15. Head portion 72 of pusher bar 66 is also spaced from fasteners 21. Adjustment member 90 is secured to body portion 15 by adjustment nut 91 and has been rotated to move opposed flat 94 into position to engage the proximal end 102 of adjustment slot 98 upon advancement of pusher bar 66.

In FIG. 34, clamp slide 36 and cartridge carrier 38 have been moved to their distal-most positions as defined by adjustment member 90 to advance cartridge 22 towards anvil 20, as indicated by arrow "L". The proximal end 102 of adjustment slot 98 is spaced from opposed flat 94 of alignment member 90 to permit further distal advancement of pusher bar 66.

In FIG. 35, pusher bar 66 has been advanced to move proximal end 102 of adjustment slot 98 into engagement with opposed flat 94. Head portion 72 has engaged fasteners 21, to drive fasteners 21 into anvil 20. Although not shown, a biasing member, such as a spring, is provided to return pusher bar 66 and clamp slide 36 to retracted positions upon release of trigger actuator 64 and return of approximation clamp 34 to its pre-actuated most position.

Referring temporarily back to FIGS. 9 and 33, the adjustment mechanism of fastener applying device 10 facilitates ejection of multiple size fasteners from a single device, for example, 3.5 mm and 4.8 mm fasteners. To prevent a cartridge containing 4.8 mm fasteners from being inserted into a device set to eject 3.5 mm fasteners, cartridges 22 containing 4.8 mm fasteners are provided with a leg 158 extending from a proximal end of cartridge body 104. If adjustment member 90 is properly set to eject 4.8 mm fasteners, leg 158 will be received in recess 96 of adjustment member 90. However, if the adjustment member is set to eject 3.5 mm fasteners, a cartridge adapted to contain 4.8 mm fasteners cannot be inserted into cartridge carrier 38 because leg 158 of cartridge 22 will be obstructed by opposed flat 94.

It will be understood that various modifications may be made to the embodiments disclosed herein. For example, the approximating clamp 34 may be formed with more than three detents to provide a greater number of stages of approximation. The adjustment member 90 may also be provided with more than two flats offset from each other to permit ejection of a greater number of different size fasteners from a single device 10. Therefore, the above description should not be construed as limiting, but merely as exemplifications of preferred embodiments. Those skilled in the art will envision other modifications within the scope and spirit of the claims appended hereto.

What is claimed is:

1. A device for applying a plurality of surgical fasteners to body tissue, the device comprising:
   a housing having a distally extending body portion;
   an anvil and a cartridge carrier supported at a distal end of the housing for relative movement;
   an approximation mechanism operably associated with the cartridge carrier and being movable to approximate the cartridge carrier and the anvil;
   a pusher bar extending within the housing, the pusher bar being movable over a predetermined stroke to effect ejection of fasteners from a cartridge positioned in the cartridge carrier; and
   an adjustment member operably associated with the pusher bar to selectively vary the stroke of the pusher bar to accommodate ejection of different size fasteners from the device.

2. A device according to claim 1, wherein the adjustment member is movable to different positions of engagement with respect to the pusher bar to selectively vary the stroke of the pusher bar.

3. A device according to claim 2, wherein the adjustment member includes at least two abutment surfaces, the adjustment member being movable to selectively position the abutment surfaces for engagement with the pusher bar.

4. A device according to claim 3, wherein the pusher bar includes an adjustment slot having a stop surface, the adjustment member extending through the adjustment slot and being movable to selectively position one of the abutment surfaces for engagement with the stop surface.

5. A device according to claim 4, wherein the adjustment member includes a rotatable shaft.

6. A device according to claim 5, wherein the at least two abutment surfaces are formed as circumferentially spaced recesses on a periphery of the rotatable shaft.

7. A device according to claim 1, wherein the pusher bar includes a plurality of integrally formed distally extending fingers, the pusher bar being movable with respect to the cartridge carrier to engage and effect ejection of fasteners from a cartridge positioned in the cartridge carrier.

8. A device according to claim 7, further including a cavity formed in the distal end of the pusher bar, wherein the pusher bar is constructed of plastic and a metal support plate is positioned in the cavity.

9. A device according to claim 1, further comprising an alignment mechanism including lateral and longitudinal alignment members operably connected to the approximation mechanism to align the cartridge carrier and the anvil during approximation of the anvil and the cartridge carrier.

* * * * *